United States Patent [19]
Hamlin et al.

[11] Patent Number: 5,849,499
[45] Date of Patent: Dec. 15, 1998

[54] MONOCLONAL ANTIBODY TO ACETYLATED LYSINE RESIDUES IN RECOMBINANT BOVINE SOMATOTROPIN

[75] Inventors: Diane Marie Hamlin, Otsego; Gustavus Adolphus Walker, Portage, both of Mich.

[73] Assignee: Pharmacia & Upjohn Company, Kalamazoo, Mich.

[21] Appl. No.: 830,431

[22] Filed: Feb. 3, 1992

Related U.S. Application Data

[63] Continuation of Ser. No. 389,833, Aug. 4, 1989, abandoned.
[51] Int. Cl.$^6$ ............................ C07K 16/00; G01N 33/53
[52] U.S. Cl. ............................ 435/7.1; 435/7.2; 435/336; 530/388.1; 530/388.24
[58] Field of Search ............................ 530/388.1, 388.24; 435/240.2, 172.2, 7.1, 7.2, 7.6, 336

[56] References Cited

PUBLICATIONS

Muller et al., *Mol. Immunol.*, v. 24, 1987, pp. 779–789.
Steinbrecher et al., *J. Lipid Res.*, v. 25, 1984, pp. 1109–1116.
Biological Abstracts, vol. 83, (11), 1987, p. ab–345, biosciences information services phil. Kriwi, G. et al.: "Antigenic Regions of Bovine . . . " abstracte number 106644–see abstract.
Journal of Biological Chemistry, vol. 261, No. 6, (Feb. 25, 1986), Baltimore US, pp. 2496–2498;Ulrich Pfeffer et al.: "Availbility of Hyperacetylated H4 Histone in Intact Nucleosome to Specific Antibodies".
S. Muller et al, 1987, Molecular Immunology 24:779–789, "Specificity of Antibodies Raised Against Triacetylated Histone H4".
G. Piperno et al, 1985, J. Cell. Biol. 101:2085–2094, "Monoclonal Antibodies Specific for an Acetylated Form of –Tubulin Recognize the Antigen in Cilia and Flagella from a Veriety of Organisms".
U. Pfeffer et al, 1985, J. Biol. Chem., 261:2496–2498, "Availability of Hyperacetylated H4 Histone in Intact Nucelosomes to Specific Antibodies".
U. P. Steinbrecher et al, 1984, J. Lipid Research, 25: 1109–1115, "Immunogenicity of Homologous Low Density Lipoprotein After Methylation, Ethylation, Acetylation or Carbamylation: Generation of Antibodies Specific For Derivatized Lysine".

*Primary Examiner*—Frank C. Eisenschenk
*Attorney, Agent, or Firm*—Gregory W. Steele; James D. Darnley, Jr.; Thomas A. Wootton

[57] ABSTRACT

Provided are hybridomas for producing monoclonal antibodies against acetylated lysine residues of rbSt. The antibodies are specific to the presence of at least a single acetylated lysine in a protein and can differentiate between α-acetyl and ε-acetyl lysine as free amino acids.

5 Claims, No Drawings

MONOCLONAL ANTIBODY TO ACETYLATED LYSINE RESIDUES IN RECOMBINANT BOVINE SOMATOTROPIN

CROSS-REFERENCE TO RELATED APPLICATIONS

This application is a continuation of international application PCT/US90/03879 filed 16 Jul. 1990, which was a continuation application of U.S. Ser. No. 07/389,833 filed 4 Aug. 1989, now abandoned.

FIELD OF THE INVENTION

This invention relates to hybridoma technology and the production of monoclonal antibodies using that technology. More specifically, the invention relates to hybridomas that produce monoclonal antibodies directed against acetylated lysine residues in heterologous polypeptides, specifically, recombinant bovine somatotropin (rbSt), the monoclonal antibodies produced thereby, and methods for using said monoclonal antibodies for the detection and quantitation of acetylated lysine residues of rbSt.

BACKGROUND OF THE INVENTION

The acetylation of lysine residues in native proteins i.e., proteins normally produced in an organism, is a post-translational modification introduced by a host organism (Allfrey, V. G., et al., 1983, "Post-translational Covalent Modification of Proteins", ed. B. Conner Johnson, (Academic Press, NY), pp. 181–199; Wold, F., 1981, Annual Rev. Biochem., 50:783). This phenomenon has been studied in histones (Muller, S., et al., 1987, Molecular Immunology 24:779); Chlamydomonas α-tubulin, (Piperno, G., et al., 1985, J. Cell Biol. 101:2085; L'Hernault, S. W., et al., 1985, Biochem. 24:473; L'Hernault, S. W., et al., 1983, J. Cell Biol. 97:258); and low density lipoproteins (LDL) (Steinbrecker, U. P., et al., 1984, J. Lipid Research 25:1109).

Recombinant bovine somatotropin i.e., bovine somatotropin produced by recombinant DNA methods or rbSt is important for the increased lactation and growth of cattle. rbSt has been reported to be acetylated primarily at the lysine residues in positions 157, 167, 171 and 180 (see U.S. application Ser. No. 07/323,901, filed 15 Mar. 1989, which is incorporated herein by reference). Acetylation, in addition to other rbSt impurities (e.g. rbSt having substituted iso-aspartic acid for asparagine at amino acid residue 99 and deamidation), causes a shift of the protein isoelectric point (pI) from 8.2 to 7.0. The acetylated form of rbSt accounts for 67% of the pI 7.0 band of rbSt or 15–30% of the total rbSt produced in a fermentation. Furthermore, published studies indicate that chemical acetylation of lysines in human growth hormone and bovine growth hormone decreases or inhibits somatogenic receptor binding of the molecules (Teh, L. C., et al., 1988, Biochem. Biophys. Res. Comm. 150:391; de la Llosa, P., et al., 1985, Febs. Letters 191:211; and Martal, J., et al., 1985, Febs. Letters 180:295), making them less desirable as veterinary agents. Therefore, an efficient and effective method for testing rbSt for the presence and amount of acetylated lysines is desirable. It would also be desirable to purify acetylated rbSt from the non-acetylated native species.

Previous studies described the production of monoclonal antibodies (MABs) which bind to diacetylated, monoacetylated and nonacetylated histone H4 and the production of antisera containing polyclonal antibodies which react to tri and diacetylated H4 (See Muller, supra). MABs specific for an acetylated form of α-tubulin have been reported (See Piperno, supra). Antibodies which specifically recognized the tetra-acetylated form of H4 histone have also been prepared, (Pfeffer, U., et al., 1985, J. Biol. Chem. 261:2496) as well as antibodies generated against acetylated LDL (Steinbrecher, supra).

The presence of acetylation would be easier to detect if an antibody specific for the acetylated lysine residue itself, regardless of the amount of acetylation, were available.

INFORMATION DISCLOSURE

Although the presence and location of acetylated lysines in a protein can be determined by N-terminal sequencing and Fast atom bombardment (FAB) mass spectrometry, these methods are not amenable for routine quantitation of acetylated impurities in protein lots produced by recombinant DNA methods.

Several monoclonal and polyclonal antibodies have been developed for routine protein modification analysis and quantification. Muller et al., discussed above, obtained ten MABs by immunizing mice with triacetylated histone H4. None of these MABs is completely specific for acetylated forms of H4 and they do not show a detectable reaction to triacetylated H4. Muller further teaches an antisera which strongly reacts to tri and diacetylated H4. The Muller antibodies are specific to H4. They do not crossreact with other acetylated proteins. Muller et al. do not refer to recombinant proteins generally and more particularly, rbSt.

Piperno et al., discussed above, refer to seven MABs that appear to be specific for an acetylated form of α-tubulin. However, none of the antibodies recognize acetylated lysine alone. They require the presence of the α-tubulin molecule. Piperno et al. say nothing about MABs relating to rbSt or to recombinant proteins generally.

Pfeffer et al., discussed above, teach a polyclonal antibody which can be used to identify specific regions of chromatin. The antibody recognizes the tetra-acetylated form of H4. However, it does not crossreact with other acetylated proteins, and Pfeffer et al. do not teach MABs.

Steinbrecher et al., discussed above, also teach a polyclonal antibody specific for an acetylated lysine. It does not relate to MABs. It does not crossreact with recombinant proteins, and it does not relate to rbSt.

SUMMARY OF THE INVENTION

The present invention provides:

(1) A hybridoma which produces monoclonal antibodies against acetylated lysine residues of recombinant bovine somatotropin;

(2) A hybridoma as described above which is ATCC# HB-10181;

(3) A monoclonal antibody to acetylated lysine residues of recombinant bovine somatotropin which can differentiate between α-acetyl and ε-acetyl groups in a free lysine amino acid;

(4) A monoclonal antibody as described above which is a monoclonal antibody against a recombinant bovine somatotropin having acetylated lysine residues;

(5) A monoclonal antibody as described above produced by hybridoma ATCC# HB-10181;

(6) A monoclonal antibody as described above which is of the class IgG;

(7) A method for determining the percentage of acetylation in recombinantly produced bovine somatotropin comprising the steps of:

a) contacting monoclonal antibodies against acetylated lysine residues of recombinant bovine somatotropin to the rbSt sample;
b) maintaining said monoclonal antibodies in contact with said recombinant bovine somatotropin for a time and under conditions sufficient for the formation of immunological complexes between said monoclonal antibodies and acetylated lysine residues of recombinant bovine somatotropin;
c) detecting the quantity of said immunological complexes resulting from said contact;

(8) A method as described above wherein:
a) as a first step, immobilizing the recombinant bovine somatotropin sample on a solid support;
b) contacting the monoclonal antibodies with the immobilized recombinant bovine somatotropin sample;
c) maintaining the monoclonal antibodies in contact with the immobilized recombinant bovine somatotropin for a time and under conditions sufficient to allow formation of a first immunological complex;
d) detecting the first immunological complex by removing the monoclonal antibodies not immunologically complexed with the immobilized recombinant bovine somatotropin, contacting a second antibody with the first immunological complex, the second antibody comprising an indicator for detection, maintaining the second antibody in contact with the first immunological complex for a time and under conditions sufficient to allow formation of a second immunological complex, removing the second antibody not immunologically complexed with the first immunological complex, and detecting the second immunological complex.

(9) A method as described above wherein the monoclonal antibody against acetylated lysine residues of recombinant bovine somatotropin is produced by hybridoma ATCC# HB-10181.

DETAILED DESCRIPTION OF THE INVENTION

The acetylation of lysines in recombinant bovine somatotropin (rbSt) is an impurity in recombinant proteins introduced as a post-translational modification by the host *E. coli*. Although the presence and location of acetylated lysines in a protein can be determined via N-terminal sequencing and FAB-mass spectrometry, these methods are not amenable for routine quantification of acetylated impurities in recombinant protein lots. The present invention offers a simple and effective means to routinely screen and quantify rbSt lots to determine the amount of this lysine acetylation for purposes of quality control.

The monoclonal antibody defined as a single antibody produced by a hybridoma cell, is produced by immunization of CAF/J mice with chemically acetylated rbSt. The acetylation of rbSt is accomplished using acetic anhydride. Standard hybridoma procedures are followed to isolate the IgG MABs. The preferred method is to use acetylated rbSt which has been purified from a production lot of rbSt prepared in *E. coli*.

Quantitation of acetylated rbSt (pI 7.0) is accomplished using an indirect, noncompetitive Enzyme-linked immunosorbent assay (ELISA). The rbSt sample is immobilized on a polystyrene microtiter plate and the MAB is added to the plate. Bound MAB is detected by peroxidase-labelled rabbit anti-mouse IgG.

The specificity of any MAB of the invention can be characterized by chemically acetylating various synthetic rbSt peptides and evaluating them as inhibitors in a competitive ELISA.

The present invention is exemplified in more detail in the examples below.

EXAMPLE 1

Part A. Chemical Acetylation of Recombinant Bovine Somatotropin

A rbSt sample is chemically acetylated using established procedures. See, e.g., (Means, G. E., et al., 1971, Chemical Modifications of Proteins, Holden Cay, Inc., Oakland, Calif., pg. 214 and Fraenkel-Conrat, H., 1959, Methods Enzymology 4:247). Approximately 10 mg rbSt in 0.1 ml water is mixed with 0.1 ml saturated sodium acetate buffer, pH 9.6 (Sigma). To solubilize the protein, 0.12 gm of guanidine hydrochloride (Gdn—HCl) (Schwarz/Mann Biotech) is added, giving a final concentration of 6M Gdn—HCl. The mixture is cooled on ice for thirty minutes. 2 $\mu$l of acetic anhydride (Mallinckrodt) is added every 10 minutes for one hour at 0° C.

The acetic anhydride and Gdn—HCl are removed by dialysis against phosphate buffered saline (PBS) for 48 hours at 4° C. The chemically acetylated rbSt is lyophilized and stored at −20° C. Synthetic rbSt peptides comprising various fragments of the rbSt molecule are similarly acetylated.

Part B. Purification of pI 7.0 Recombinant Bovine Somatotropin

The pI 7.0 fraction of rbSt is isolated/purified by chromato-focusing. Thirty ml of swollen PBE-94 gel (Pharmacia) is packed in a 1×30 cm column and equilibrated/washed with 12 bed volumes ($\approx$300 ml) of 0.025M ethanolamine-acetate buffer, pH 9.4. A 15.4 mg/ml solution of rbSt in the ethanolamine buffer is added to the PBE column and eluted at a flow rate of 26 ml/hr with a 1/10 dilution of Polybuffer-96 (Pharmacia). Fractions (1.5 ml each) are collected (ISCO Fraction Collector) in glass tubes, with protein detection by UV monitor ($A_{280}$, ISCO). The column is regenerated using 2–3 bed volumes ($\approx$100 ml) of 1.0M sodium chloride (NaCl). The pI 7.0 fractions are pooled and the polybuffer ampholytes are removed by ammonium sulfate precipitation. The ammonium sulfate ($NH_4SO_4$) is added as a solid to the pI 7 fraction to 90% saturation at 25° C. The solution is stirred for 2 hours at room temperature and then centrifuged at 3,2000 rpm (Sorval). The precipitate is washed three times with saturated $NH_4SO_4$ solution and centrifuged each time at 10,000 rpm. The final precipitate is reconstituted in 0.1M $NaHCO_3$, pH 9.5 and dialyzed against the same buffer overnight at 4° C. The purified pI 7.0 rbSt is aliquoted into 1.5 ml Eppendorf capped centrifuge tubes and stored at −20° C. The protein concentration of the purified pI 7.0 was determined by spectrophotometry at 280 nm using a coefficient of 1.46 to be 6.3 mg/ml. Isoelectric focusing (IEF) analysis of the purified pI 7.0 indicated a cluster of four dark bands at pI 6.7–7.2, with the majority concentrated at pI 6.9–7.0, and a series of faint bands from pI 5.8–6.7. This reagent, "purified pI 7.0", is composed of rbSt impurities (e.g. acetylated, deamidated, and/or Iso-Asp-99 forms rbSt) that cause a shift in protein pI from 8.2 to 7.0 region.

Other versions of both purified pI 7.0 rbSt and purified pI 8.2 rbSt are isolated from a rbSt lot produced with glycine substituted for the normal asparagine in position 99 (See U.S. patent application Ser. No. 07/299,107, filed 19 Jan. 1989, incorporated by reference herein). This substitution prevents the base-catalyzed rearrangement of the asparagine to iso-aspartate-99 (i.e., Iso-Asp-99 rbSt impurity). The pI 7.0 fraction from this fermentation, "gly-99 pI 7.0", consists of the acetylated and deamidated forms of rbSt. "Gly-99 pI 8.2" is the corresponding pI 8.2 fraction. The two proteins are supplied as lyophilized solids and reconstituted in appropriate buffer.

Isoelectric focusing of rbSt, purified pI 7.0, gly-99 pI 7.0 and gly-99 pI 8.2 is accomplished using the PHAST IEF system (Pharmacia). Protein samples (3 μl of 2–3 mg/ml solutions) in PBS are applied onto pre-cast 0.35 mm polyacrylamide PhastGel IEF pH 3–9 gels (Pharmacia) and isoelectric focused for 520 VH (1910 V/2.5 mA/35 W/15° C). A broad pI calibration kit, pH 3–10 (Pharmacia), is used as pI standards to define the pH gradient. To visualize the presence and location of the separated proteins, IEF gels are directly stained by the fast Coomassie blue staining method outlined in the PhastSystem Development Technique No. 200.

Part C. Production of Monoclonal Antibodies $CAF_1/J$ mice (Jackson Laboratories) are immunized with 50 μg chemically acetylated rbSt emulsified in Freund's complete adjuvant (Difco) intraperitoneally (IP). Second and third boosters are administered IP at 4 week intervals using 25 μg chemically acetylated rbSt in Freund's incomplete adjuvant. Final boosting involves IV injection of 10 μg purified pI 7.0 rbSt dissolved in PBS (10 mM $NaPO_4$, 150 mM NaCl, pH 7.3) four days prior to the somatic cell hybridization. Spleenocytes obtained from the immunized mouse with the highest titer of anti-acetylated rbSt are fused with a SP-2/0 mouse plasmacytoma cell line following established techniques (Lane, R. D., 1985, J. Immunol. Methods 8:223). Cultures producing acetylated rbSt (pI 7.0) and pI 8.2 specific immunoglobulins are detected using a screening ELISA and cloned to single cell per well status by standard limiting dilution in microtiter plates (Corning). Select positive wells are recloned to insure monoclonality and isotyped (as $IgG_1$) using an established Particle Concentration Fluorescence Immunoassay (PCFIA) method. Monoclonal antibody producing hybridomas of interest are expanded in culture and stock solutions are frozen for long-term cryopreservation of the cell lines.

Ascites fluids are produced for the anti-pI 7 and anti-pI 8.2 monoclonal cell lines by injecting $CAF_1/J$ mice IP with 0.5 ml of Pristane (2,6,10,14-tetramethylpentadecane; Sigma Chemical Co.). Seven days later, $10^7$ monoclonal hybridoma cells are injected IP into the mice. Ascites fluid is collected 1–2 weeks later.

The anti-pI 7 and anti-pI 8.2 monoclonal antibodies are purified from the murine ascites fluid by ammonium sulfate fractionation, followed by protein A chromatography. Initially, 8 ml saturated ammonium sulfate (Sigma) at 4° C. is added dropwise to 8 ml of ascites fluid and allowed to stir on ice for 1 hour. The suspension is centrifuged at 13,000 rpm in a microcentrifuge (Model 5415, Brinkman Instruments). The pellet is resuspended in 8 ml PBS and dialyzed overnight against 0.05 mM $Na_2PO_4$ at pH 8.5.

For the protein A chromatography, 5 ml of swollen Affigel-Protein A (Bio-Rad Labs) is packed into a 1×10 cm column (Bio-Rad) and washed with 25 ml of pH 9.0 Bio-Rad binding buffer (prepared as 31.4 gm per 100 ml deionized/distilled water). Six ml of dialyzed sample is mixed with an equal volume of binding buffer and applied to the column. The column is washed with 50 ml of binding buffer. The MAB is eluted by addition of pH 3.0 Bio-Rad elution buffer (prepared as 2.2 gm per 100 ml deionized, distilled water) and collected as 2 ml fractions (ISCO Fraction Collector) with protein detection via UV monitor ($A_{280}$; ISCO). After this purification procedure is repeated for each of the ascites samples, the eluted fractions for the anti-pI 7 and anti-pI 8.2 MAB are separately pooled, neutralized to pH 7 with 1M Tris buffer, pH 9.0, and concentrated/dialyzed in a Micro-Prodicon Concentrator (Biomolecular Dynamics). The protein concentrations of the purified anti-pI 7 and anti-pI 8.2 MABs are determined by $\Sigma^1{}_{2\cdot 8}{}^4{}_0{}^6$ to be 11.4 mg/ml and 6.6 mg/ml, respectively. The purified MABs are dispensed into 0.5 ml micro-Eppendorf capped centrifuge tubes (Bio-Rad) and stored at –20° C.

The specificity of the purified anti-pI 7 and anti-pI 8.2 MABs is verified using a screening ELISA which indicated titers of 1:1,600,000 and 1:10,000, respectively. The anti-pI 7 and anti-pI 8.2 MABs are further characterized and shown to exhibit heavy (≈50,000 daltons) and light (≈22,000 daltons) antibody chains when subjected to sodium dodecyl sulfate-polyacrylamide gel electrophoresis (SDS-PAGE). Upon IEF testing, a cluster of 4–6 bands is observed for each MAB with average pIs of 5.8±0.16 and 6.4±0.16 for the anti-pI 7 and anti-pI 8.2 MABs, respectively.

EXAMPLE 2

Part A. Characterization of the Anti-pI Antibody

The anti-pI 7 MAB functions best if the rbSt or purified pI 7.0 rbSt is immobilized on a solid support (microtiter plate, nitrocellulose) or if the gly-99 pI 7.0 rbSt is used as an inhibitor in solution. rbSt, as the inhibitor in solution with the anti-pI 7 MAB, will not compete against either itself or gly-99 pI 7 immobilized on the plate, even at a concentration of 1000 μg/ml. Similar results occur when purified pI 7.0 rbSt is used as the inhibitor in solution. In contrast, gly-99 pI 7.0 provides mean 50% inhibition points of 2.4 μg/ml and 18.8 μg/ml against gly-99 pI 7.0 and rbSt respectively. The rbSt/purified pI 7.0 will compete only when Nonidet P-40 (NP-40), a nonionic detergent which perturbs protein conformation, is incorporated in the solution phase. In the presence of 0.5% NP-40, rbSt competes against purified pI 7.0 immobilized on the plate (50% inhibition point of 500 μg/ml), while no inhibition occurs without NP-40, even at 2000 μg/ml rbSt. Furthermore, the gly-99 pI 8.2 rbSt does not interact with the anti-pI 7 MAB, regardless of the presence or absence of the NP-40.

1. Immunoblot

Immunoblot analysis of the anti-pI 7 and anti-pI 8.2 MABs is accomplished using established procedures (Hamilton, R. G. et al., 1987, Hybridoma 6:205; Jonsdottir, I. et al., 1984, Febs. Letters 167:15; and PhastSystem Development Technique File, No. 220, 1987, Pharmacia Phastsystem Owner's Manual, Tryckkontakt, Uppsala, Sweden). For the diffusion blotting, nitrocellulose (Bio-Rad) is cut to a size slightly larger than the IEF gel, pre-soaked 5 min. in PBS and carefully overlaid onto the IEF gel excluding all air bubbles. A piece of blotting (thick) filter paper (Bio-Rad is subsequently placed on top of the nitrocellulose and the entire gel-nitrocellose-blotting paper assembly is flipped over (blotting paper down) onto a gel dryer (Bio-Rad) for overnight incubation under vacuum at room temperature.

For the immunoassay, the nitrocellulose is peeled from the gel and blocked with 0.05% Tween-20 (Bio-Rad) in PBS, pH 7.3, for two hrs at room temperature on a rotating platform shaker (American Lab). Following three washes in PBS, the nitrocellulose is incubated with undiluted anti-pI 7 MAB or anti-pI 8.2 MAB cell culture supernatant for two hours at room temperature with constant agitation. The membrane is washed three times in PBS, immersed in peroxidase-labelled goat anti-mouse Ig diluted 1:2000 in PBS and agitated for two hours at room temperature. After three washes in PBS, the bound MAB is detected by incubating the nitrocellulose for 30 minutes at room temperature in freshly prepared DAB substrate (0.5 mg/ml 3-3'diaminobenzidine (Sigma) and 0.5 $\mu$l/ml 30% $H_2O_2$ in citrate-$PO_4$ buffer. The buffer contains 29.4 gm sodium citrate dihydride and 13.8 gm $NaH_2PO_4$ $H_2O$ per liter, pH to 7.5). The reaction is stopped by rinsing the membrane in $H_2O$ and air-drying. The anti-pI 7 MAB is bound to the pI 7 and more acidic bands in the pI 7 and rbSt samples, but exhibited no reactivity with the pI 8–8.2 bands of rbSt or gly-99 pI 8.2 samples. In contrast, the anti-pI 8.2 MAB cross-reacted with both the pI 8.2 and pI 7 bands in all samples.

2. Indirect, Noncompetitive ELISA

Quantitation of the acetylated rbSt (pI 7.0) is accomplished using an indirect, noncompetitive ELISA, with the rbSt sample immobilized on the polystyrene microtiter plate and the bound MAB detected by peroxidase-labelled rabbit anti-mouse IgG. Standard curves of the immobilized protein (e.g. pI 7, pI 8.2, rbSt, chemically acetylated rbSt) are prepared by initially diluting the protein to 20 $\mu$g/ml in bicarbonate buffer, pH 9.6. This solution is 2-fold serially diluted in polyethylene centrifuge tubes (Corning) using bicarbonate buffer and the dilution is subsequently transferred to respective columns in Immulon II microtiter plates, using 100 $\mu$l per well. The appropriate dilution (1:3000) of the peroxidase anti-mouse IgG conjugate is determined by testing various concentrations and selecting one which gives maximum (most sensitive) OD values for the rbSt standard curve, while exhibiting a background (negative control) response in the absence of bound antibody of LT 0.1 OD.

The assay is linear over a range of 0.15–2.5 $\mu$g/ml. The referenced rbSt contained ≈32% pI 7.0, with a relative standard deviation (RSD) of 13%. Ten different rbSt lots are assayed against the reference one each of three days and provide results ranging from 21.3–38.7% pI 7.0, with an average RSD of 6.8%.

3. Competitive ELISA

The specificity/epitope characterization of the MAB is studied by chemically acetylating various synthetic rbSt peptides and evaluating them as inhibitors in a competitive ELISA. Wells of Immulon II microtiter plates are coated with 10 $\mu$g/ml solutions of either purified pI 7.0 or rbSt and subsequently blocked using 1% gelatin Bio-Rad) in PBS, pH 7.3, for 1.5 hours at room temperature. An appropriate initial concentration of the inhibitor (usually 1–10 mg/ml, depending upon supply) is prepared in bicarbonate buffer (15 mM $Na_2CO_3$, 35 mM $NaHCO_3$, pH 9.6) and 2-fold serially diluted using the same buffer in polypropylene centrifuge tubes containing 1% gelatin-PBS buffer (usually 2.0 ml per tube and/or the volume necessary to provide a 1:10 dilution of the inhibitor). A 1.6 $\mu$g/ml solution of anti-pI 7 MAB is prepared in 1% gelatin-PBS and aliquots (usually 250 $\mu$l each) are transferred to each of the tubes containing inhibitor-1% gelatin-PBS mixtures. The tubes are vortexed and allowed to incubate at room temperature for 45 min. The appropriate MAB dilution was selected as the concentration giving an OD of ≈1.0 in the absence of an inhibitor. Negative controls for the assay involve substituting either normal mouse serum (NMS) or 1% gelatin-PBS for the anti-pI 7 MAB and bicarbonate buffer for the inhibitor. The assay positive consists of the anti-pI 7 MAB in solution without an inhibitor (only bicarbonate buffer added). Following the 45 min. incubation, the MAB-inhibitor solutions are transferred (100 $\mu$l per well) to respective columns of blocked and washed microtiter plates containing immobilized purified pI 7 or rbSt. The plates are incubated two hours at room temperature. After three washes, 100 $\mu$l of peroxidase-labelled anti-mouse IgG (Southern Biotech) diluted 1:3000 in 1% gelatin-PBS is added to each well which is for two hours at room temperature. The plate is washed 4 times prior to the detection of bound antibody by adding 200 $\mu$l per well of 0.4 mg/ml Ortho-phenylenediamine (Sigma) in 0.1M citrate-K2HPO4 buffer, pH 4.5, containing 0.4 $\mu$l/ml of 30% $H_2O_2$ (Mallinckrodt). After incubation in the dark at room temperature for 30 min., the reaction is stopped by addition of 50 $\mu$l per well of 2.5M $H_2SO_4$ (Mallinckrodt). The optical densities of the wells are measured at 490 nm on a microtiter plate reader (Model EL310, Biotek) linked to an IBM-PCXT clone (Fountain) for data storage and analysis.

The inhibitors consist of acetylated versus nonacetylated versions of various synthetic rbSt peptides and commercial peptides containing single lysine groups with different neighboring amino acids. The synthetic rbSt peptides are made according to Merrifield, R., 1963, J. Amer. Chem. Soc. 85:2154. Xenopsin, elodoisin and serum thymic factor (STF) are purchased from Chemalog; neurotensin, both bradykinins, lysine, $\alpha$-acetyl lysine and $\epsilon$-acetyl lysine come from Sigma; and Serva supplies the "Fo-phe-met-phe-lys".

The synthetic rbSt peptide inhibitors and their 50% inhibition points in decreasing order of response are: rbSt amino acid residues 152–177 (0.39 $\mu$g/ml)>rbSt amino acid residues 130–150 (7.8 $\mu$g/ml)>rbSt amino acid residues 179–191 (18.8 $\mu$g/ml). The degree of inhibition correlates with the number of acetylated lysine residues. The normal, nonacetylated forms of these peptides do not compete in the assay, even at 500 $\mu$g/ml. To further clarify the epitope, various commercial peptides containing single lysines with different neighboring amino acids are acetylated and evaluated as inhibitors. The data indicates that the MAB is not only specific to the presence of at least a single acetylated lysine residue in a protein, but can also differentiate between $\alpha$-acetyl versus $\epsilon$-acetyl-lysine as free amino acids.

The preferred hybridoma and monoclonal antibody of the instant invention are produced by hybridoma VH25-1E5-2D1-2B8 (pI 7.0 or acetylated lysine antibody), designated as UC® HB-21 and deposited in accordance with the requirements under the Budapest Treaty on the International Recognition of the Deposit of Microorganisms for the Purposes of Patent Procedure at the American Type Culture Collection, 12301 Parklawn Drive, Rockville, Md. 20852, USA, on 14 Jul. 1989 under accession number HB-10181.

We claim:

1. A method of determining the percentage of acetylation in recombinant bovine somatotropin comprising the steps of:
    a) contacting monoclonal antibodies against a recombinant bovine somatotropin having acetylated lysine residues with a recombinant bovine somatotropin sample;
    b) maintaining the monoclonal antibodies in contact with the recombinant bovine somatotropin for a time and under conditions sufficient to allow formation of immunological complexes between the monoclonal antibodies and the recombinant bovine somatotropin; and
    c) detecting the quantity of the immunological complexes.

2. A method according to claim 1 wherein:
a) as a first step, immobilizing the recombinant bovine somatotropin sample on a solid support;
b) contacting the monoclonal antibodies with the immobilized recombinant bovine somatotropin sample;
c) maintaining the monoclonal antibodies in contact with the immobilized recombinant bovine somatotropin for a time and under conditions sufficient to allow formation of a first immunological complex;
d) detecting the first immunological complex by removing the monoclonal antibodies not immunologically complexed with the immobilized recombinant bovine somatotropin, contacting a second antibody with the first immunological complex, the second antibody comprising an indicator for detection, maintaining the second antibody in contact with the first immunological complex for a time and under conditions sufficient to allow formation of a second immunological complex, removing the second antibody not immunologically complexed with the first immunological complex, and detecting the second immunological complex.

3. A method according to claim 1 wherein the monoclonal antibody against recombinant bovine somatotropin acetylated lysine residues is produced by hybridoma ATCC# HB-10181.

4. A hybridoma which is ATCC HB-10181.

5. A monoclonal antibody produced by ATCC HB-10181.

* * * * *